(12) United States Patent
Joergensen et al.

(10) Patent No.: US 8,100,856 B2
(45) Date of Patent: Jan. 24, 2012

(54) BALLOON CATHETER

(75) Inventors: Ib Joergensen, Haigerloch (DE);
Andrew Jeffrey, Tubingen (DE);
Suk-Woo Ha, Langwiesen (CH)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 0 days.

(21) Appl. No.: 10/511,911

(22) PCT Filed: Apr. 22, 2003

(86) PCT No.: PCT/EP03/04149
§ 371 (c)(1),
(2), (4) Date: Aug. 18, 2005

(87) PCT Pub. No.: WO03/089037
PCT Pub. Date: Oct. 30, 2003

(65) Prior Publication Data
US 2006/0004328 A1 Jan. 5, 2006

(30) Foreign Application Priority Data
Apr. 22, 2002 (DE) .................... 102 17 868

(51) Int. Cl.
*A61M 31/00* (2006.01)
*A61M 29/00* (2006.01)

(52) U.S. Cl. .......... 604/103.09; 604/103.04; 604/96.01; 606/194

(58) Field of Classification Search ............... 604/96.01, 604/103.04, 103.09, 915, 917, 921; 606/191, 606/192, 194; 623/1.11
See application file for complete search history.

(56) References Cited

U.S. PATENT DOCUMENTS

| 4,545,390 A | | 10/1985 | Leary |
|---|---|---|---|
| 4,597,755 A | | 7/1986 | Samson et al. |
| 4,748,982 A | | 6/1988 | Horzewski et al. |
| 4,762,129 A | | 8/1988 | Bonzel |
| 4,771,777 A | | 9/1988 | Horzewski et al. |
| 4,775,371 A | * | 10/1988 | Mueller, Jr. ................. 606/192 |
| 4,798,598 A | | 1/1989 | Bonello et al. |
| 4,922,923 A | | 5/1990 | Gambale et al. |
| 4,943,278 A | | 7/1990 | Euteneuer et al. |
| 4,944,745 A | | 7/1990 | Sogard et al. |
| 4,953,553 A | | 9/1990 | Tremulis |
| 4,960,410 A | * | 10/1990 | Pinchuk .................... 604/96.01 |
| 5,470,322 A | | 11/1995 | Horzenwski et al. |
| 5,820,612 A | | 10/1998 | Berg |
| 5,951,494 A | * | 9/1999 | Wang et al. .................. 600/585 |
| 6,152,914 A | | 11/2000 | Van De Kerkhof et al. |

(Continued)

FOREIGN PATENT DOCUMENTS
CA 2183214 2/1998
(Continued)

*Primary Examiner* — Jackie Ho
*Assistant Examiner* — Victoria P Campbell
(74) *Attorney, Agent, or Firm* — Workman Nydegger

(57) ABSTRACT

The invention discloses a balloon catheter comprising a catheter shaft, at the distal end of which an inflatable balloon is arranged and at the proximal end of which a connecting piece is arranged, comprising a guiding wire which can be passed through a guiding wire lumen of the catheter shaft from the proximal end to the distal end and through the balloon and an inflation or deflation lumen extending from the proximal end of the catheter shaft to the balloon, wherein a portion of the catheter shaft having a selectable length and extending from the proximal end is provided with a metal reinforcing pipe.

16 Claims, 2 Drawing Sheets

U.S. PATENT DOCUMENTS

| | | |
|---|---|---|
| 6,217,566 B1 | 4/2001 | Ju et al. |
| 6,273,879 B1 | 8/2001 | Keith et al. |
| 6,544,224 B1 * | 4/2003 | Steese-Bradley ........ 604/103.06 |
| 6,596,217 B1 * | 7/2003 | Davis-Lemessy et al. ... 264/400 |
| 6,746,423 B1 * | 6/2004 | Wantink ................... 604/103.04 |
| 2002/0072730 A1* | 6/2002 | McGill et al. ................. 604/525 |
| 2003/0050600 A1* | 3/2003 | Ressemann et al. ..... 604/101.01 |
| 2004/0054349 A1* | 3/2004 | Brightbill ..................... 604/524 |
| 2004/0102719 A1* | 5/2004 | Keith et al. ................... 600/585 |
| 2004/0121037 A1* | 6/2004 | Rouns et al. ................. 425/515 |

FOREIGN PATENT DOCUMENTS

| | | |
|---|---|---|
| DE | 8806818 | 6/1989 |
| DE | 19607595 | 9/1997 |
| DE | 69504175 | 2/1999 |
| DE | 19823064 | 11/1999 |
| EP | 0365993 | 5/1990 |
| EP | 0380873 | 8/1990 |
| WO | WO92/03178 A | 3/1992 |
| WO | WO 03/089037 | 10/2003 |

* cited by examiner

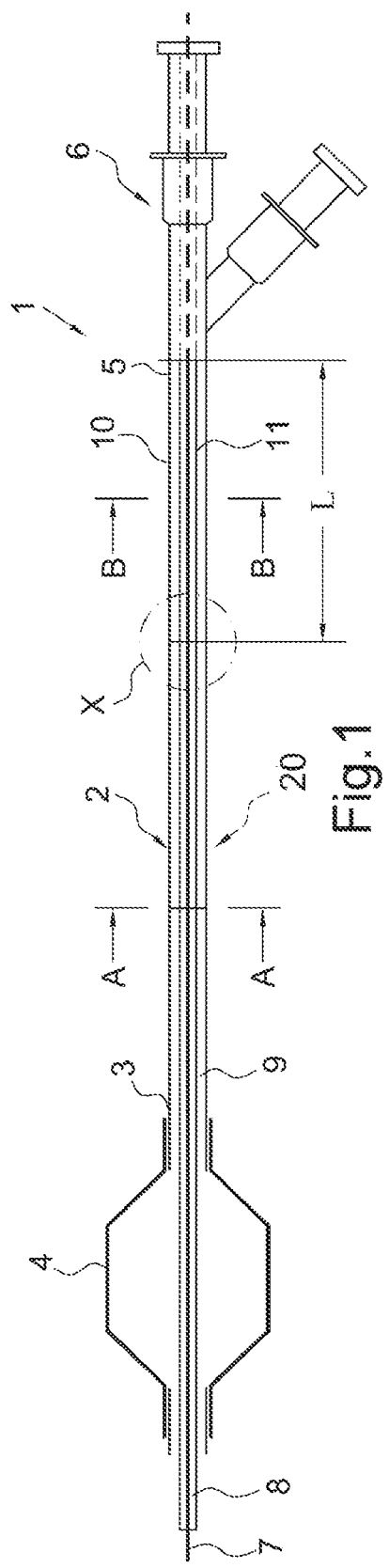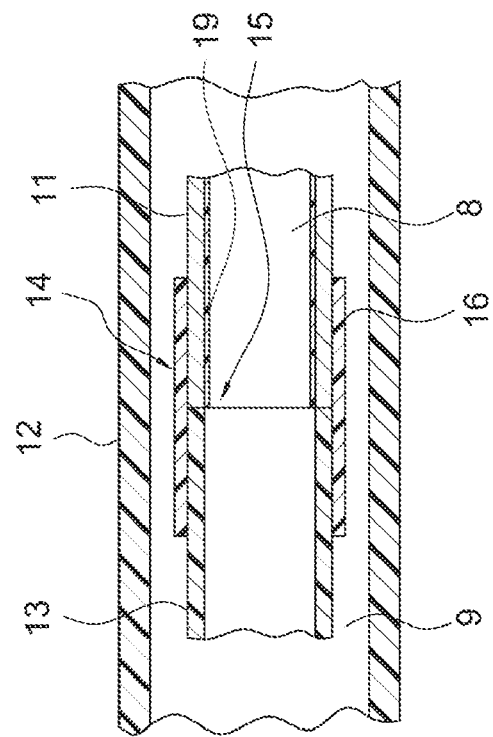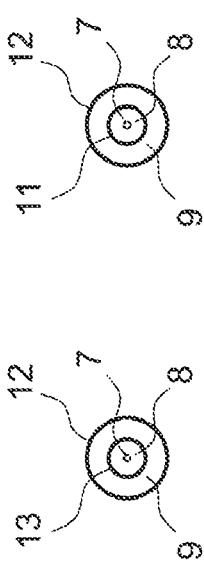

BALLOON CATHETER

BACKGROUND OF THE INVENTION

1. Field of the Invention

This invention relates to a balloon catheter suited for use with a guiding wire that passes through a guiding wire lumen of the catheter shaft from the proximal to the distal end and through a balloon.

2. Background Information

A catheter that has a guiding wire that passes through a guiding wire lumen of the catheter shaft is referred to as a so-called "over-the-wire catheter". This catheter construction comprises a catheter shaft having an inflatable balloon at its distal end. At the opposite proximal end, normally a connecting piece is arranged. Further, the known catheter comprises a guiding wire extending through a guiding wire lumen of the catheter shaft from the proximal end to the distal end and through the balloon. Finally, an inflation or deflation lumen is provided in the catheter shaft, said lumen extending from the proximal end of the catheter shaft to the balloon. Air or liquid may be supplied or discharged through said lumen for expanding the balloon.

If such a balloon catheter is to be inserted into a heart artery, an outer guiding catheter is at first pushed with its curved tip through the aorta, usually starting from the thigh, to the heart artery to be treated, in which e.g. a stenosis exists, which shall be expanded by the balloon catheter and possibly stabilized by a simultaneously implanted stent. The tip of the guiding catheter is thereby temporarily fixed in the region of the branching of the heart artery to be treated from the arch of the aorta. Into said guiding catheter, the guiding wire is subsequently inserted until its tip has passed the stenosis. In the following, the catheter shaft of the balloon catheter is inserted through the guiding wire into the aorta and the vessel to be treated, until the balloon stops in the region of the stenosis.

For this type of balloon catheter, the guiding wire must have approximately the double length of the catheter, as the catheter at first has to be threaded on the guiding wire outside the patient's body.

In a further known balloon catheter construction, a catheter shaft is provided having a shaft portion extending from the connecting piece and being composed of metal, which has a full cross section except for the inflation. Said portion (also referred to as hypotube) is followed by a plastics portion extending to the balloon in which a guiding wire volume is provided besides the inflation volume, which, however, has an outlet opening in front of the metal shaft portion, said outlet opening being positioned relatively close in front of the balloon. This makes it possible to use a substantially shorter guiding wire. In addition, this type of catheter shows a higher stiffness due to the metal shaft portion disposed in the proximal region, which enhances the so-called pushability.

SUMMARY OF THE INVENTION

It is an object of the present invention to provide a balloon catheter of the over-the-wire type having a higher pushability.

This object is solved by providing a portion of the catheter shaft with a selectable length that extends from the proximal end and that is provided with at least one reinforcing pipe.

Due to the fact that the inventive catheter has a catheter shaft portion the length of which is selectable and which extends from the proximal end, said portion being provided with a reinforcing pipe, there results at first a clearly enhanced pushability and the advantage that the friction between the guiding wire and the catheter shaft is clearly decreased. This makes the handling of the inventive catheter much more easier. It is also preferred to cover the inner periphery of a reinforcing pipe made of metal, preferably steel, with a coating which further decreases the friction, e.g. a coating made of PTFE.

In a particularly advantageous embodiment of the inventive catheter having a metal reinforcing pipe, the metal pipe may be covered inside with a coating in order to decrease the static and dynamic friction for the guiding wire. Said coating may consist of plastics, e.g. polyethylene, PTFE or Teflon.

For the purpose of coating, it is possible to mount a plastics tube, e.g. made of polyethylene, having a diameter slightly larger than the inner recess of the reinforcing pipe onto a stiletto, with or without an influence of heat, until the outer diameter of the tube is smaller than the inner diameter of the metal reinforcing pipe. The tube is introduced to the inside with the help of the stiletto and applied to the inner wall of the reinforcing pipe by a longitudinal heating due to the corresponding expansion of the pipe. Both ends of the tube are twisted off or cut off after removal of the stiletto.

In a further, particularly advantageous embodiment, the plastics tube may be cross-linked with radiation before removal, in order to achieve a better restoration of the tube in the reinforcing pipe.

In a further embodiment, the surface of the plastics tube is modified prior to its insertion into the metal reinforcing pipe for increasing the adherence at the inner wall, e.g. by plasma treatment or corona treatment.

In addition, the tube for the plastics coating may be co-extruded from e.g. polyethylene and provided with an outer adhesive layer made e. g. from ethylene vinyl acetate (EVA) or nylon.

In an alternative embodiment, the plastics tube is melted onto the inner wall of the metal reinforcing pipe using heated compressed air.

In order to obtain a better joining of the reinforcing pipe and the plastics coating, an adhesive may additionally be introduced between the inner wall of the reinforcing pipe and the tube along the overall length of the reinforcing pipe or at its ends.

In a further embodiment, it is possible to allow the inner coating to exceed the portion of the metal reinforcing pipe to cover also the adjacent portion of the plastics pipe. In an extreme case, it is possible to coat the complete inner wall of the metal reinforcing pipe and the adjacent plastics pipe.

All in all, the coatings first and foremost serve to decrease the friction between the inner wall of the respective pipe portion and the guiding wire.

In order to avoid kinks, it is further possible to provide a nylon tube coating in the transitional region between the metal reinforcing pipe and the plastics pipe.

These and other details, features and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure:

FIG. 1 is a schematically simplified view of the principle of the inventive catheter;

FIG. 2 is a sectional view along line A-A;

FIG. 3 is a sectional view along line B-B,

FIG. 4 is an enlarged view of detail X;

DETAILED DESCRIPTION OF THE PREFERRED EMBODIMENTS

Figure 5:
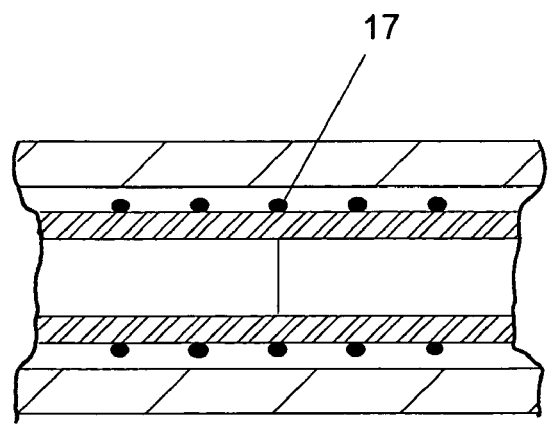
FIG. 5 is a cutaway view of an alternative embodiment of a catheter.

A selected embodiment of the present invention will now be explained with reference to the drawings. It will be apparent to those skilled in the art from this disclosure that the following description of the embodiment of the present invention is provided for illustration only and not for the purpose of limiting the invention as defined by the appended claims and their equivalents.

In FIG. 1, a balloon catheter 1 is disclosed. The catheter 1 comprises a catheter shaft 2. An inflatable balloon 4 is provided at the distal end 3 of the catheter shaft 2. A connecting piece 6 is provided at the proximal end 5 of the catheter shaft 2.

Furthermore, FIG. 1 shows a guiding wire 7 extending through the connecting piece 6 into a guiding wire lumen 8 of the catheter shaft 2 from the proximal end 5 until the distal end 3 and through the balloon 4.

In addition, an inflation or deflation lumen 9 is provided, which extends from the connecting piece 6 through the catheter shaft 2 until the balloon 4.

As shown in FIG. 1, the catheter shaft 2 comprises a portion 10 extending from the proximal end 5, said portion being provided with a reinforcing pipe 11 made of metal or plastics. It is also possible that the reinforcing pipe is made of metal and is provided with an inner coating 19 made of plastics, which is preferable for decreasing friction.

FIG. 2 shows a cross-sectional view explaining the concentric arrangement of the aforementioned lumen 8 and 9 as well as the pipes 12 and 13 limiting said lumen. In this portion of the catheter shaft 2, the pipes 12 and 13 are formed as plastics pipes, wherein the lumen 9 is disposed between the pipes 12 and 13 and the lumen 8 is disposed within the pipe 13 through which the guiding wire 7 is passed.

FIG. 3 explains the sectional view along line B-B in FIG. 1. Herein, the reinforcing pipe 11 made of metal, preferably steel such as stainless steel, is shown, said reinforcing pipe being surrounded by the plastics pipe 12 for limiting the lumen 9 in this region.

FIG. 4 shows detail X of FIG. 1 more clearly.

Figure 6:
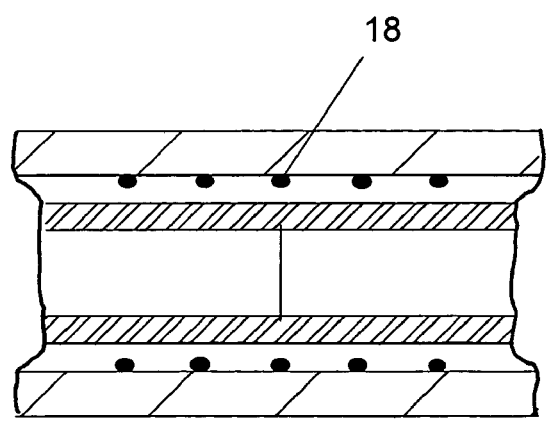
FIG. 6 is a cutaway view of a further alternative embodiment of a catheter.

The outer pipe 12 surrounds a transitional portion 15 between the reinforcing pipe 11 and the adjacent inner plastics pipe 13. Said transitional portion 15 is provided with a kink protection 14 being formed, in this example, as a sleeve 16. In variants of the present embodiment, illustrated in FIGS. 5 and 6, kink protection 14 is provided as a metal spring 17 surrounding the transitional portion, and as a metal spring 18 arranged in the inflation/deflation lumen in the area of the transitional portion.

As an alternative to the embodiments of FIGS. 1 to 4, it is conceivable that the portion 10 as a whole is formed as a metal pipe, i.e. not consisting of two concentric pipes, as shown in FIGS. 3 and 4. In this case, the metal pipe 11 has a massive cross section in which a longitudinal borehole is made for forming the lumen 8 and an adjacent borehole is made for forming the lumen 9. In another embodiment which is basically conceivable, the plastic pipe (which would correspond to the portion 20 being designated with a dotted arrow in FIG. 1) ensuing the metal pipe is also formed as a pipe with a massive cross section, in which corresponding boreholes are provided for the continuation of lumen 8 or 9.

The invention claimed is:

1. A balloon catheter comprising:
a catheter shaft having a distal end, an inflatable balloon disposed on the distal end, a proximal end coupled to a connecting piece, a guiding wire lumen extending between the proximal and distal ends within the catheter shaft, and an inflation lumen extending from the connecting piece to the inflatable balloon,
the guiding wire lumen being formed within the catheter shaft and from a proximal metallic reinforcing pipe having a selectable length and a separate distal plastics pipe extending distally from and being fixably connected to a reinforcing pipe distal-most end, the proximal metallic reinforcing pipe and the separate distal plastics pipe fluidly sealing the inflation lumen from the guidewire lumen, the inflation lumen being formed between an exterior surface of the proximal metallic reinforcing pipe and the distal plastics pipe and an interior surface of the catheter shaft,
the proximal metallic reinforcing pipe and the distal plastics pipe each being made of a solid material, the material of the proximal metallic reinforcing pipe being more rigid than the material of the distal plastics pipe,
wherein a transitional portion, transitioning the guidewire lumen from the proximal metallic reinforcing pipe to the distal plastics pipe, between the proximal and distal pipes being provided with kink protection overlapping and being fixably connected to the proximal and distal pipes.

2. The balloon catheter according to claim 1, wherein the transitional portion comprises the abutting ends of the proximal metallic reinforcing pipe and the distal plastics pipe.

3. The balloon catheter according to claim 1, wherein the kink protection comprises a sleeve.

4. The balloon catheter according to claim 1, wherein the kink protection comprises a metal spring.

5. The balloon catheter shaft according to claim 4, wherein the metal spring is arranged in the inflation lumen.

6. The balloon catheter according to claim 1, wherein the proximal metallic reinforcing pipe has a lubricity-enhancing coating.

7. The balloon catheter according to claim 1, wherein the proximal metallic reinforcing pipe includes a plastic tube applied to the inner wall of the proximal portion of the pipe.

8. The balloon catheter according to claim 7, wherein the outer surface of the plastic tube is modified by plasma treatment or corona treatment for increasing adherence at the inner wall of the proximal portion of the pipe.

9. The balloon catheter according to claim 7, wherein the plastic tube is provided with an outer adhesive layer.

10. The balloon catheter according to claim 7, wherein the plastic tube extends beyond the proximal portion and into at least a portion of the distal portion.

11. The balloon catheter according to claim 1, further comprising a nylon tube coating within the transitional portion, the nylon tube coating extending at least partially within the proximal and distal portions.

12. A balloon catheter comprising:
a catheter shaft having a distal end including an inflatable balloon and a proximal end coupled to a connecting piece, the catheter shaft comprising separate first and second boreholes extending longitudinally within at least a portion of the catheter shaft, the first and second boreholes extending from the proximal end toward the distal end, the first longitudinal borehole defining a guiding wire lumen and the second longitudinal borehole defining an inflation lumen that provides fluid communication between the connecting piece and the inflatable balloon, the guide wire lumen being formed within the catheter shaft by a proximal metallic reinforcing pipe having a selectable length and a separate distal plastics pipe extending distally from and being fixably connected to a reinforcing pipe distal-most end, the proximal metallic reinforcing pipe and the separate distal plastics pipe fluidly sealing the inflation lumen from the guidewire lumen, the proximal metallic reinforcing pipe comprising a material having a greater rigidity than the distal plastics pipe, and a transitional portion, transitioning the guidewire lumen from the proximal metallic reinforcing pipe to the distal plastics pipe, between the proximal and distal pipes being provided with kink protection overlapping and being fixably connected to the proximal and distal pipes.

13. The balloon catheter according to claim 12, wherein at least the first borehole in the catheter shaft has enhanced lubricity.

14. A balloon catheter comprising:

a catheter shaft having a distal end including an inflatable balloon and a proximal end coupled to a connecting piece, the catheter shaft comprising a guide wire lumen extending from the proximal end to the distal end, the guide wire lumen being formed within the catheter shaft from a proximal metallic reinforcing pipe and a separate distal plastics pipe disposed end to end with a distal-most end of the proximal metallic reinforcing pipe abutting a proximal end of the distal plastics pipe, the distal plastics pipe extending distally from the distal-most end of the proximal metallic reinforcing pipe, the proximal metallic reinforcing pipe and the separate distal plastics pipe fluidly sealing the inflation lumen from the guidewire lumen, the proximal metallic reinforcing pipe being fixably connected to the distal plastics pipe at a transition, the proximal metallic reinforcing pipe including a friction reducing plastic tube disposed within the proximal metallic reinforcing pipe, and a kink protection being disposed about the transition and at least partially overlapping and being fixably connected to the proximal and distal pipes, and an inflation or deflation lumen disposed between an exterior surface of the proximal metallic reinforcing pipe and the distal plastics pipe and an interior surface of the catheter shaft.

15. The balloon catheter according to claim 14, further including a lubricity-enhancing coating disposed in the guide wire lumen.

16. The balloon catheter according to claim 14, wherein the kink protection comprises a metal spring.

* * * * *